US007567651B2

(12) United States Patent
Serceki et al.

(10) Patent No.: US 7,567,651 B2
(45) Date of Patent: Jul. 28, 2009

(54) DIRECTIONAL ANTENNA SYSTEM FOR WIRELESS X-RAY DEVICES

(76) Inventors: Zeljko John Serceki, 356 Westlynn Ct., Hartland, WI (US) 53029; Daniel White Sexton, 1435 Orlyn Dr., Niskayuna, NY (US) 12309

( * ) Notice: Subject to any disclaimer, the term of this patent is extended or adjusted under 35 U.S.C. 154(b) by 673 days.

(21) Appl. No.: 11/278,140

(22) Filed: Mar. 30, 2006

(65) Prior Publication Data
US 2007/0260134 A1    Nov. 8, 2007

(51) Int. Cl.
*H05G 1/28* (2006.01)
(52) U.S. Cl. .............................. 378/162; 378/165
(58) Field of Classification Search ............... 378/1, 378/4, 19, 62, 63, 98.8, 101, 119, 16, 165, 378/210; 250/370.09, 370.11; 382/128, 382/132; 600/407
See application file for complete search history.

(56) References Cited

U.S. PATENT DOCUMENTS

| | | | |
|---|---|---|---|
| 6,823,039 B2 * | 11/2004 | Hoheisel et al. | 378/19 |
| 7,381,964 B1 * | 6/2008 | Kump et al. | 250/370.11 |
| 2003/0048770 A1 | 3/2003 | Proctor, Jr. | |
| 2004/0114535 A1 | 6/2004 | Hoffmann et al. | |
| 2004/0130487 A1 | 7/2004 | Hoffmann et al. | |
| 2005/0146470 A1 | 7/2005 | Li et al. | |
| 2006/0023839 A1 * | 2/2006 | Shoji | 378/97 |
| 2007/0270660 A1 * | 11/2007 | Caylor et al. | 600/300 |

* cited by examiner

*Primary Examiner*—Irakli Kiknadze
(74) *Attorney, Agent, or Firm*—William Baxter; Ellis B. Ramirez; Michael G. Smith (57) ABSTRACT

Systems and techniques are provided for a directional antenna system that employs a wireless link between x-ray apparatus. The system includes a host computer, an x-ray tube with an emission scan channel, a first directional antenna connected to the x-ray tube and with an orientation parallel to the emission channel, a second antenna wirelessly communicating with the first directional antenna, an x-ray detector wirelessly communicating with the x-ray tube, and a rigid panel supporting the second antenna and the x-ray detector being in contact with the emission scan channel. Specific techniques are employed to manage antenna direction and transmission.

14 Claims, 5 Drawing Sheets

DIRECTIONAL ANTENNA SYSTEM FOR WIRELESS X-RAY DEVICES

BACKGROUND OF THE INVENTION

1. Field of Invention

This invention relates generally to wireless x-ray devices, and more particularly to wireless x-ray devices employing a directional antenna system.

2. Description of Related Art

Conventional wireless systems are becoming more prevalent with applications that previously had to operate with wired connections. Wireless technology includes applications spanning single peer-to-peer connections, to broadly diverse wireless networks (e.g., WLAN). Further, wireless systems operate in conjunction with environments that support more than one discrete wireless system, and must therefore be able to effectively operate within the wireless confluence and the available wireless resources, (e.g., communication bandwidth).

In these conventional wireless systems, the individual wireless signals oftentimes interfere with each other. Further, wireless signals also compete with non-wireless sources that by virtue of an electric current source affect localized electromagnetic fields.

Wireless systems are becoming more prevalent in the medical field. One use of wireless technology in the medical field frees the patient from being tied or tethered to medical monitoring equipment. The portability and movement of both patients and the diagnostic and testing equipment associated with patient care is greatly simplified with wireless sensors for testing and diagnostic equipment. Wireless systems allow patients to be monitored during extended evaluation periods and allow for the data to be more representative of a patient's "real life". Wireless systems use antennae to transmit information by emitting electromagnetic waves, measured in radio frequency units, typically between 10 kHz and 10 GHz.

One problem with a wireless system is interference, either passive created by a physical obstacle or obstruction, or active which is created by another signal source. With a wireless system in use at a medical facility, the system must contend with a large number of both physical and active obstacles. Additionally, the wireless system must be able to operate with unobtrusive antennae, and typically with power from a standard internal wall outlet.

Equipment of all kinds in a medical facility must be held to the strictest standards of performance and reliability, otherwise any use of the equipment must be discontinued for fear of placing the patients at risk. With wireless technology allowing patient monitoring, and data transfer, the technical limitations and boundaries of wireless systems have been closely examined. However, the physical phenomena of interference and attenuation of RF signals or waves provided physical constraints, not the actual data.

With medical radiology, whereby a patient undergoes an x-ray, both the technician and the patient are exposed to radiation during the imaging procedure. Clearly, it is beneficial to both the patient and the technician not to repeat an x-ray session. However, oftentimes a problem with the patient's orientation during the x-ray imaging procedure is not apparent until after the imaging procedure is completed and the x-rays are viewed.

One problem with conventional x-ray systems is improper patient positioning that prevents the radiologist or technician from successfully imaging the desired areas. Improper patient placement can also create passive interference that will affect the wireless signals traveling between a transmitter and a receiver. Although x-rays will travel through a patient's body, radio frequency (RF) micro-wavelength signals will not pass through the patient's body. In fact, as with any solid object the RF signals will be reflected off the patient's body and oftentimes such reflection will redirect the signals away from the intended receiver's location. In addition to the redirection caused by signal reflection, the original signal will also undergo attenuation, or loss of power typically measured in decibels (dB), as a result of the reflection.

Further, another aspect with conventional x-ray systems is the lack of any real time-of-session feedback concerning the necessary strength of the x-ray beam required to successfully image the target area of a patient. X-rays, even in small amounts, cause damage to living tissues. Obviously, current measures are taken to protect both a patient undergoing a radiology examination and the technician operating the equipment. Unfortunately, oftentimes a radiologist must insure complete imaging at the cost of boosting the strength of the radiation beam. Although the radiologist will adjust the strength of the radiation beam, power adjustments made to the radiology equipment prior to, or during the session are done with only general operational understanding.

Further, with the increasing costs associated with medical care, more efficient use of the radiology equipment and the staff's time would be desirable. Obviously, the best case for efficiency would have no inaccurate or unusable x-rays.

Accordingly, it is an object of the present invention to provide a wireless x-ray system whose operation minimizes any interference both to and from the wireless x-ray system and any other operating networks or systems.

It is another object of the present invention to assist with the proper placement and positioning of a patient for a targeted radiology session.

It is further another object of the present invention to assist with the signal transmission and acquisition for a wireless antenna array.

It is further another object of the present invention to provide a transmission power control technique to further reduce potential interference with other wireless devices.

SUMMARY OF THE INVENTION

The foregoing problems are solved and the foregoing objects are achieved in accordance with the following illustrative embodiments of the invention in which a directional antennae system is deployed with a license-free, low power wireless link for use with x-ray equipment. Additionally, the characteristics of wireless signal transmission are utilized to balance the effects of a radiological procedure. Further, proper balancing and management of the radiological procedure will generate the minimum amount of x-ray radiation during a radiological examination.

DETAILED DESCRIPTION OF THE PREFERRED EMBODIMENT

Figure 1:
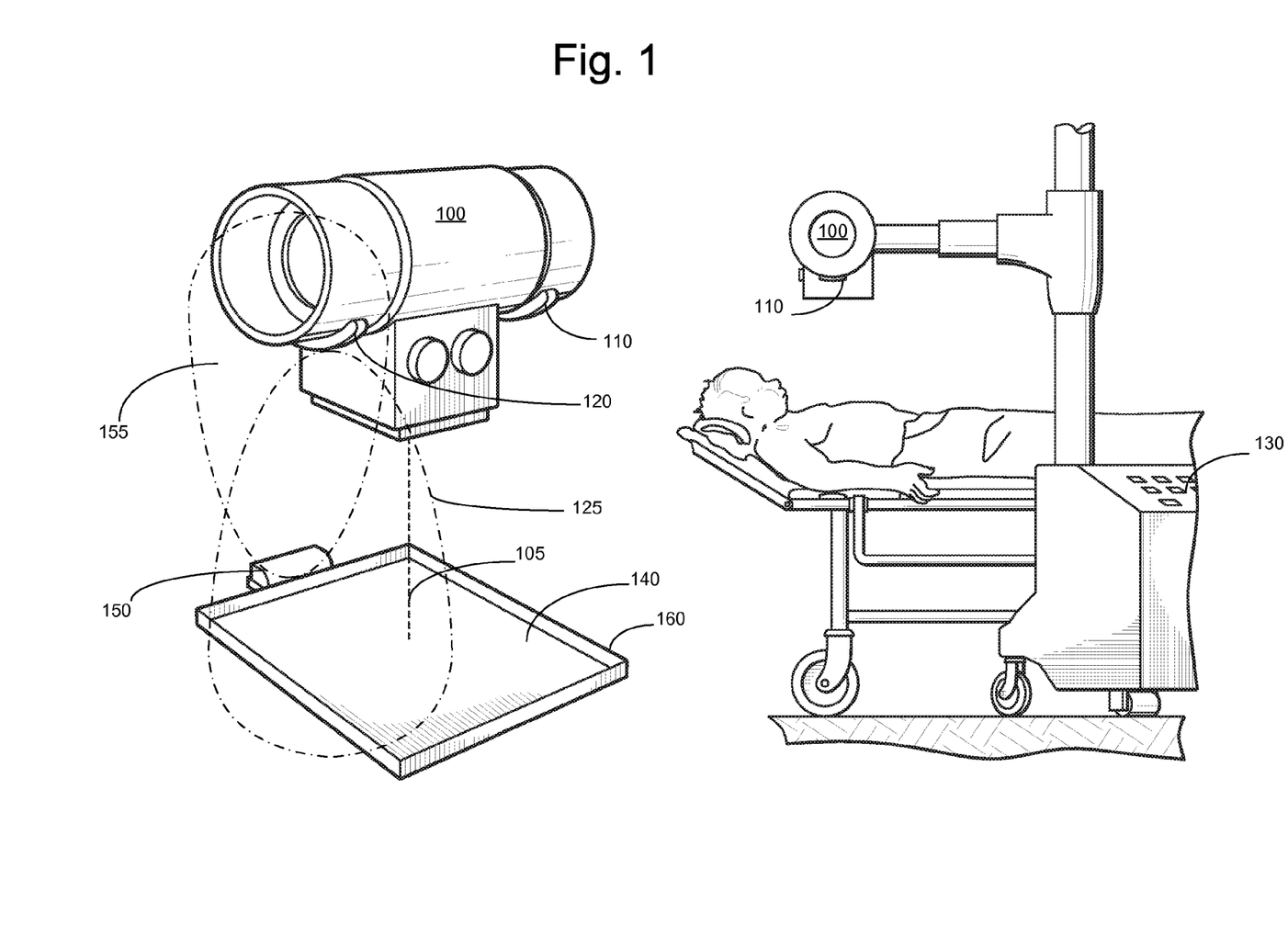
FIG. 1 is a side perspective view of an exemplary embodiment of the inventive directional antenna system.

FIG. 1 is a side perspective view of an exemplary embodiment of the directional antenna system according to this invention. The x-ray tube 100 is connected via a communications link 115 to a host computer system 130. The x-ray tube 100 has two directional antennae 110 and 120, attached to the x-ray tube's body, with their respective locations along the two terminating ends of the x-ray tube 100. Each of the two directional antennae 110 and 120 is positioned proximate to either end of the x-ray tube's body, and relative to communicate with a wireless x-ray detector 140.

The wireless x-ray detector 140 has a third directional antenna 150 located below the x-ray tube 100 and relative to communicate with each of the two directional antennae 110 and 120. The two directional antennae 110 and 120 send signals in a primary transmission pattern downward and away from the x-ray tube 100. The single directional antenna 150 sends signals in a primary transmission pattern upward and away from the wireless x-ray detector 140.

In a first embodiment of the invention, the directional antennae system only uses one directional antenna (either 110 or 120) that are attached to the body of the x-ray tube 100. The one directional antenna, 110 or 120, attached to the body of the x-ray tube 100, would transmit (send RF energy) towards the wireless x-ray detector 140. The transmitted RF signal from directional antenna 110 or 120 would be received by the single directional antenna 150.

As shown in FIG. 1, the directional antenna 120 has a primary transmission path 125. Additionally, the directional antenna 150 has a primary transmission path 155. The wireless x-ray detector 140 may be located on a panel 160 that is placed beneath the radiology patient. Further, the directional antenna 150 may be located on panel 160. The position of the directional antenna 150 may be for example, on the periphery of the panel 160, at such a location where a radiology patient would not block or otherwise interfere with the directional antenna 150.

The wireless x-ray detector 140 is contained within or upon the panel 160. As shown in FIG. 1, the panel 160 also includes a directional antenna 150. The directional antenna 150 is oriented upward, towards the x-ray tube 100, and when active would transmit towards the x-ray tube 100.

When a user, for example a radiology technician, powers on the host computer system 130, or any other controller coupled to the inventive directional antenna system, a signal is sent to a single directional antenna, for example 120, mounted upon the x-ray tube body 100. The signal sent to the directional antenna 120 prepares the antenna's transmission carrier signal for operation. At the same time, or approximate to that time period, a signal is sent to the directional antenna 120, a separate signal is sent to directional antenna 150 mounted upon the wireless x-ray detector 140. The signal sent to the directional antenna 150 prepares the antenna's transmission carrier signal for operation.

Once the circuits supplying the carrier signals for the directional antennae have been sufficiently charged, an operator, either a human, automatic or mechanical, will initiate the directional antennae. Directional antennae are particularly useful in low-power, license-free wireless transmission environments, since a directional antenna will maximize the efficiency of a low-power, targeted transfer. A directional antenna channels the RF signal in a particular direction. These channeled RF signals form a conically-shaped lobe transmission path, as shown in FIG. 1. Directional antenna 120 has its respective signal lobe transmission path 125, and directional antenna 150 has its respective signal lobe transmission path 155. A RF signal generally gets stronger the closer one gets to the center of a given signal lobe transmission path. Therefore, the signal is the strongest at the center of the signal lobe transmission path.

In the exemplary environment, for example a medical facility, the use of a directional antenna system with a wireless system must not interfere with any of the numerous other systems wireless or wired. Since the power band available to a license-free wireless system is very limited, the system must be deployed in such a manner to minimize any interference. An optimal deployment would include unobstructed lines of sight between any pair of antennae, and with directional antennae a given communicative pair should be essentially pointed at each other.

X-ray radiology optimally operates when an irradiation beam passes straight through the target, for example a radiology patient, and perpendicularly strikes the film or other media capturing the image. Clearly the type and scale of the radiology equipment is directly proportional to the size of a specific targeted area that may be successfully imaged. The inventive concept of this disclosure is not dependent upon a specific type or scale of radiology equipment. Rather, the inventive concept of this disclosure is applicable to all known or later developed radiology equipment.

As shown in FIG. 1, the x-ray tube 100 is suspended over a subject. The x-ray tube 100 emits an x-ray beam 105 that irradiates the subject. The wireless x-ray detector 140 is located beneath the subject and receives the x-ray beam 105 after the x-ray beam has passed through the subject.

The wireless x-ray detector 140 and panel 160 are located beneath the x-ray tube 100, and essentially perpendicular to the x-ray beam 105. With the subject laid upon the panel 160, the subject is also positioned essentially perpendicular to the x-ray beam. As discussed, the panel 160 has the directional antenna 150 mounted upon it, and ideally the directional antenna 150 should have an unobstructed line of sight to the directional antenna 120 attached to the x-ray tube 100. For a mono-emission x-ray apparatus system, the equation for attenuation is represented by Beer's Law.

$$I = I_0 \exp[-\mu x], \tag{1}$$

Where $I_0$ is the initial X-ray intensity, $\mu$ is the linear attenuation coefficient for the material being scanned (units: 1/length), and x is the length of the X-ray path through the material.

As shown in FIG. 1, the placement of the directional antenna upon the x-ray tube 100 is fixed or can be readily ascertained. Further, dependent on whether the x-ray tube 100 is suspended essentially adjacent to a subject, or suspended at some distance over a subject, that spatial relationship can be readily ascertained. Still further, the linear attenuation coefficient $\mu$, for a subject is known or can be readily ascertained. Accordingly, the overall attenuation may be readily ascertained for any individual scan.

Optimal alignment of the x-ray equipment and apparatus will provide for optimal RF signaling between a pair of directional antenna of the inventive directional antenna system. Conversely, if the RF signaling is not operating at an efficient level or proximate to (efficiency defined as a function of resources consumed versus resources available) the x-ray irradiation will not be optimal.

Figure 2:
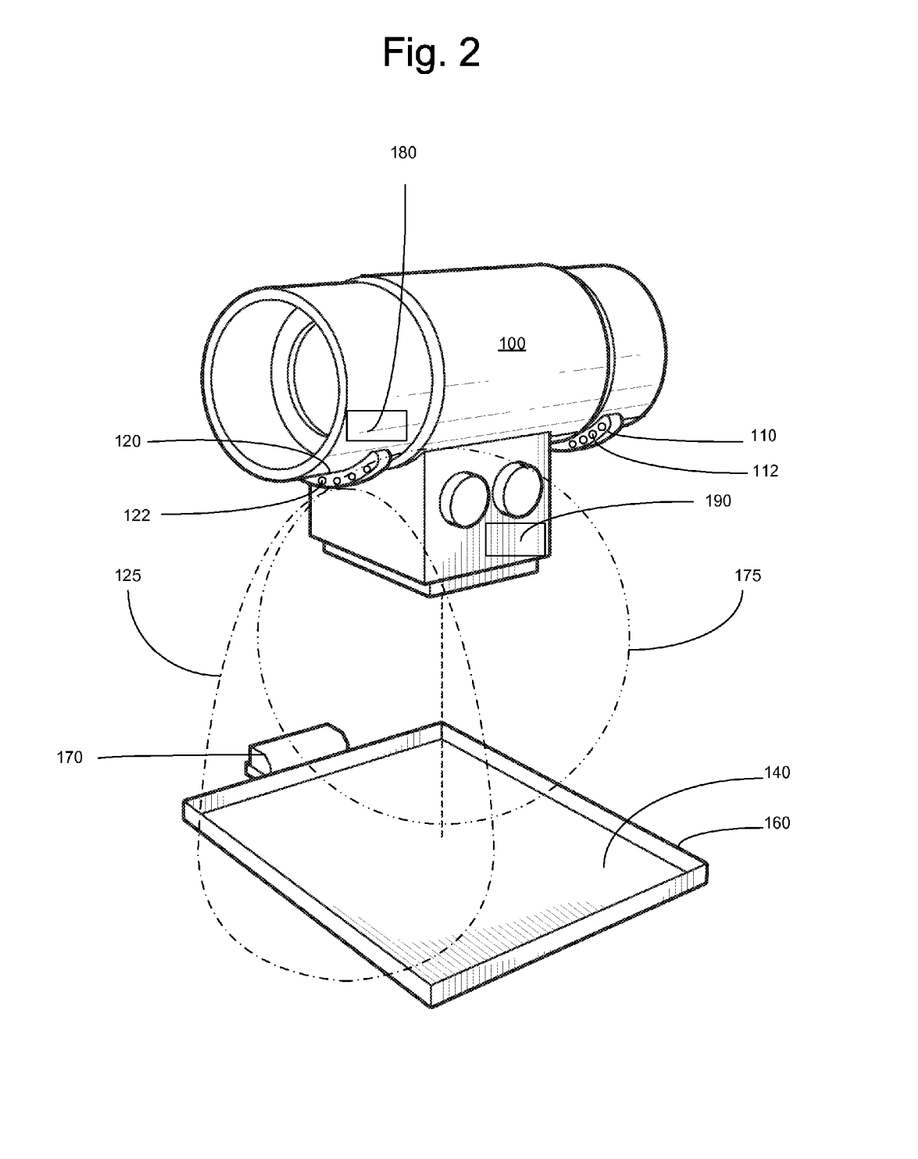
FIG. 2 is a side perspective view of a second exemplary embodiment of the inventive directional antenna system.

FIG. 2 is a side perspective view of a second exemplary embodiment of the directional antenna system according to this invention. The x-ray tube 100 is connected via a communications link 115 to a host computer system 130. The x-ray tube 100 has two directional antennae 110, and 120 attached to the x-ray tube's body, with their respective locations along the two terminating ends of the x-ray tube's 100 body. Each of the two directional antennae 110, and 120, is positioned proximate to either end of the x-ray tube's body, and relative to communicate with a wireless x-ray detector 140.

The wireless x-ray detector 140 has an omni-directional antenna 160 located below the x-ray tube 100 and relative to communicate with each of the two directional antennae 110, and 120. The two directional antennae 110 and 120 send signals in a primary transmission pattern downward and away from the x-ray tube 100. The single omni-directional antenna 160 sends signals in a transmission pattern radiating away from the wireless x-ray detector 140.

As shown in FIG. 2, the directional antenna 120 has a primary transmission path 125. Additionally, the omni-directional antenna 160 has a transmission path 165. The wireless x-ray detector 140 may be located on a panel 160 that is placed beneath the radiology patient.

In a second embodiment of the invention, the directional antenna system uses one directional antenna (either 110 or 120) that are attached to the body of the x-ray tube 100. The one directional antenna, 110 or 120, attached to the body of the x-ray tube 100, would transmit (send RF energy) towards the wireless x-ray detector 140. The transmitted RF signal from directional antenna 110 or 120 would be received by the single omni-directional antenna 170.

As shown in FIG. 2, the directional antenna 120 has a primary transmission path 125. Additionally, the omni-directional antenna 170 has a primary transmission path 175 (an omni-directional antenna generates a general, radial in all directions, expanding transmission path). The wireless x-ray detector 140 may be located on a panel 160 that is placed beneath the radiology patient. Further, the omni-directional antenna 170 may be located on panel 160. The position of the omni-directional antenna 170 may be for example, on the periphery of the panel 160, at such a location where the radiology patient would not block or otherwise interfere with the omni-directional antenna 170.

When a user, for example a radiology technician, powers on the host computer system 130, or any other controller coupled to the inventive directional antenna system, a signal is sent to a single directional antenna, for example 120, mounted upon the x-ray tube body 100. The signal sent to the directional antenna 120 prepares the antenna's transmission carrier signal for operation. At the same time or approximate to that time period, a signal is sent to the directional antenna 120 and a separate signal is sent to the omni-directional antenna 170 mounted upon the wireless x-ray detector 140. The signal sent to the omni-directional antenna 170 prepares the antenna's transmission carrier signal for operation.

Once the circuits supplying the carrier signals for the antennae have been sufficiently charged, an operator, either a human, automatic or mechanical will initiate the antennae. Directional antennae are particularly useful in low-power, license-free wireless transmission environments, since a directional antenna will maximize the efficiency of a low-power, targeted transfer. These channeled RF signals form a conically shaped lobe transmission path 125, originating from directional antenna 120.

In contrast to a conically-shaped lobe of a directional antenna, an omni-directional antenna produces an essentially radial broadcast that travels from a point of origin outwardly in 360 degrees. Further, with omni-directional antennae, the signal gets weaker the farther the signal travels from the point of origin. However, unlike a directional antenna an omni-directional antenna would be effective in applications when an essentially straight line-of-sight between the transmission source and the receiver is not available, or otherwise not certain to be available.

In the exemplary environment of a medical facility, the use of the inventive directional antenna system employing both a directional antenna and an omni-directional antenna must be deployed so not to interfere with any of the numerous other systems within the facility. Since the power band available to a license-free wireless system is very narrow, the system must be deployed in such a manner to minimize interference. Although by combining both a directional antenna and an omni-directional antenna the effects of a physical barrier, for example a radiology patient, are diminished and successful license-free wireless communication is attainable. Further, optimal deployment of a directional antenna and an omni-directional antenna pair is achieved when any portion of a radial emanating RF wave (beam) 175 from the omni-directional antenna 170 is received by the directional antenna 120.

In addition, and as shown in FIG. 2, a smart self-directing antenna may be used at the x-ray tube 100 with the inventive directional antenna system. The smart self-directing antenna subsystem may include an actuator 180 or similarly designed and operative mechanism. The actuator 180 would be coupled to the inventive directional antenna system, and further controlled by the host computer 130 or a similarly operative controller. The actuator 180 would receive signals from the host computer 130 that would include specific field parameters. These field parameters may include instructions that direct the directional antenna 120 to move to specific positions. Further, from these specific positions, the directional antenna 120 could determine if the signal source from, for example the wireless x-ray detector 140 with an omni-directional antenna 170, is serviceable. Additionally, the information gathered by the host computer 130 from the determination of whether a specific position produces a serviceable signal source, could be measured for a number of quantifiable characteristics including strength and clarity.

The smart self-directing antenna subsystem may balance the information received against specific thresholds and or ideal target goals. Once the smart self-directing antenna subsystem has determined which specific position the directional antenna 120 moved to and yielded the most desirable serviceable signal source, the smart self-directing antenna subsystem may direct the antenna actuator 180 to reposition the directional antenna 120 at that position. Further, when the antenna actuator 180 has positioned the directional antenna 120 at the most desirable position, the host computer 130 may initiate the directional antenna 120 for serviceable signal transmission and reception.

Further, and in addition to the deployment of an actuator, or in a system without the functionality of an actuator, a multi-element antenna may be included with the inventive directional antenna system. As shown in FIG. 2, the multi-element antenna 112 is found within directional antenna 110, and a multi-element antenna 122 is found within directional antenna 120. However, it should be understood that a multi-element antenna, may for example, be deployed in a proximate location to the directional antennae 110 and or 120.

For ease of illustration, this description will specifically describe multi-element antenna 122; however a similar description is explicitly implied for multi-element antenna 112. Multi-element antennae would be coupled to the inventive directional antenna system and further would be controlled by the host computer 130 or similarly tasked operative controller.

The multi-element antenna 122 would receive signals from the host computer 130 that would include specific field parameters. These field parameters may include instructions that direct the directional antenna 120 to activate a specific element or elements of the multi-element antenna 122. Further, from these specific element activations, the directional antenna 120 could determine if the signal source from, for example the wireless x-ray detector 140 with an omni-directional antenna 170, is serviceable. Additionally, the information gathered by the host computer 130 from the determination of whether specific element activation produces a serviceable signal source, could be measured for a number of quantifiable characteristics including strength and clarity.

Still further in addition, and as shown in FIG. 2, a transmission power control subsystem may be used with the inventive directional antenna system. The transmission power control subsystem may include a power controller 190 or a similarly designed or operative mechanism. It should be understood that any control subsystem may be contained either within the x-ray tube 100, or may physically reside within the host computer 130, or may be resident in some other location completely separate and distinct from any of the components and systems described and or disclosed herein. Further, the scope of this invention is not dependent upon the specific location of this control subsystem.

The power controller 190 would be coupled to the inventive directional antenna system, and further managed by the host computer 130 or a similarly operative management system. The power controller 190 would receive signals from the host computer 130 that would include specific parameters. These parameters may include instructions that direct the power controller 190 to cycle up or down a specified power band. Further, from this specific power band range, the power controller would direct the directional antenna 120, or the omni-directional antenna 170 to boost or diminish their respective signal strengths. Additionally, the direction to boost or diminish respective signal strength, would be in response to the power controller 190 determining that the specific RF signal was too small or too large and either affected the performance of other wireless devices in the area or vicinity, or did not create an optimal or near to optimal serviceable signal exchange for transmission and reception by the inventive directional antenna system.

Still further in addition, and as shown in FIG. 2, it should be understood that either the smart antenna actuator 180, and or the power controller 190, may be deployed in the inventive directional antenna system, or any such similar subsystem currently known or later developed. The scope of the inventive directional antenna system is not solely dependent upon either subsystems' deployment or operation.

Figure 3:
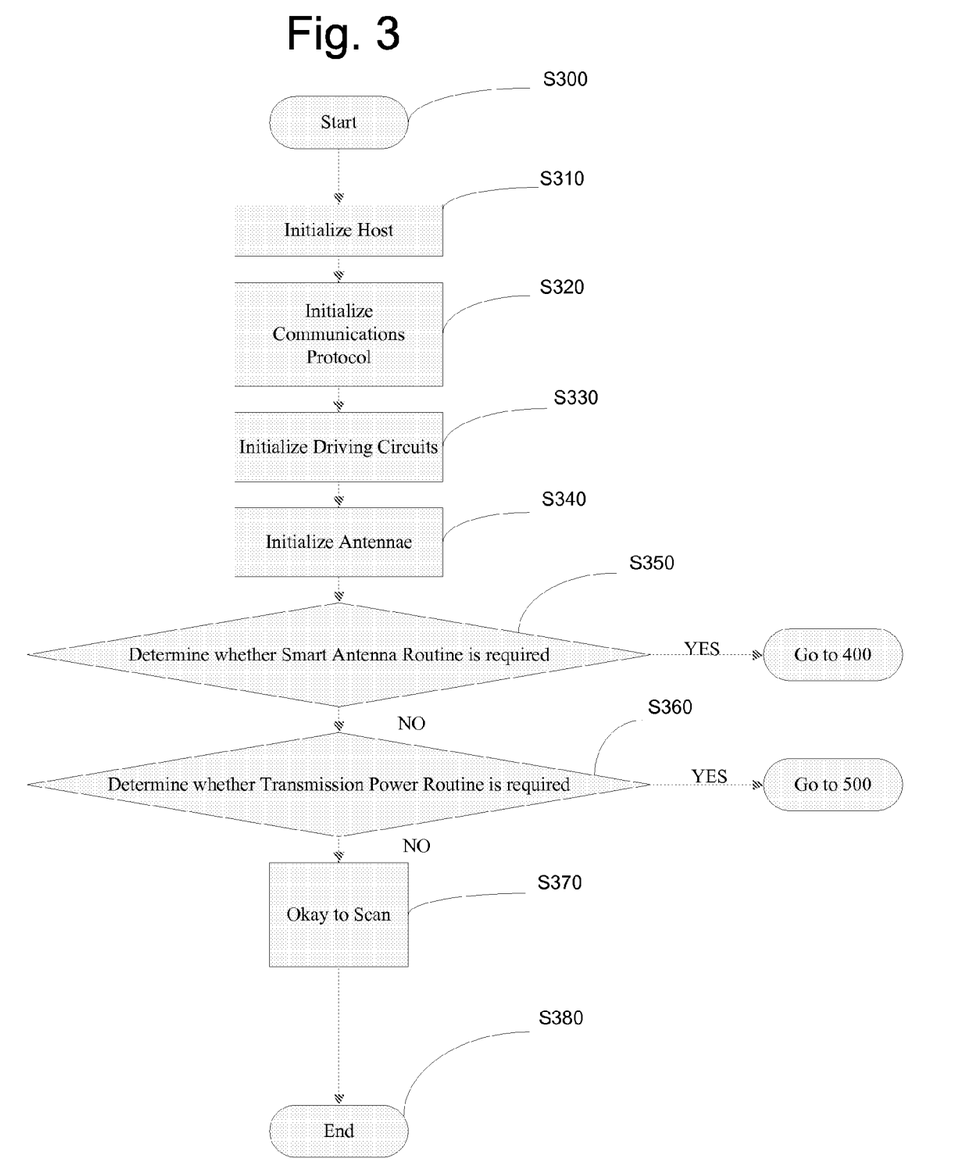
FIG. 3 is a flowchart of an exemplary method to activate the antennae according to this invention.

FIG. 3 is a flowchart of an exemplary method to activate the antennae according to this invention. As shown in FIG. 3, the process of activation of the antennae according to this invention begins at step S300 and immediately continues to step S310.

In step S310 the host computer 130, or similar processor or controller, is initialized, or otherwise activated. The initialization may occur when the processor receives a signal from any type of conventional source or triggering event. Further, the initialization may incorporate any type of conventional source or triggering event, known or later developed. After the host computer 130 has been initialized, control continues to step S320.

In step S320 the communications protocols are initialized, or otherwise activated. The communications protocols or protocol may be IEEE 802.11, or 802.11b, or some similarly effective protocol for wireless service, either currently known or later developed. After the communications protocols are initialized, control continues to step S330.

In step S330 the driving circuits, or similar device or devices, are initialized, and which initialization process may include charging by active current or potential energy held in a storage device. The driving circuits may be a conventional capacitor array, or any other similar device or means currently known or later developed. After the driving circuits are initialized, control continues to step S340.

In step S340 the antennae are initialized, or otherwise turned from an inactive state to an active state. The antennae initialization may include specific instructions directed to an individual antenna, or to a group of specific antennae, or to all the antennae within the addressable range for the inventive directional antenna system. It should be understood that antennae may include any type of antennae, including directional or omni-directional. After the antennae are initialized, control continues to step S350.

In step S350 the determination is made whether the smart antennae routine is required. The discussion of the smart antennae routine is found following the description in FIG. 4. If in step S350 the determination is made that the smart antenna routine is required, control continues to step S400. Contrary, and if the determination is not made that the smart antenna routine is required, control continues to step S360.

In step S360 the determination is made whether the transmission power routine is required. The discussion of the transmission power routine is found following the description in FIG. 5. If in step S360 the determination is made that the transmission power routine is required, control continues to step S500. Contrary, and if the determination is not made that the transmission power routine is required, control continues to step S370.

In step S370 the inventive directional antenna system will receive the signal that it is permissible to scan, or otherwise operate the x-ray equipment for a radiology session. It is not determinative concerning the scope of the inventive directional antenna system by what method or means such signal is communicated to an operator, or received by another system. Further, in step S370 a determination is made as to whether the scanning process is to be terminated. The scanning process may be terminated by a user logoff sequence, a timeout, through further control or management systems, or the like. If the scanning process is not terminated, control will jump to step S300. Steps S300-S370 are then repeated until a determination is made in step S370 that the session is to be terminated. Control then continues to step S380 and process ends.

Figure 4:
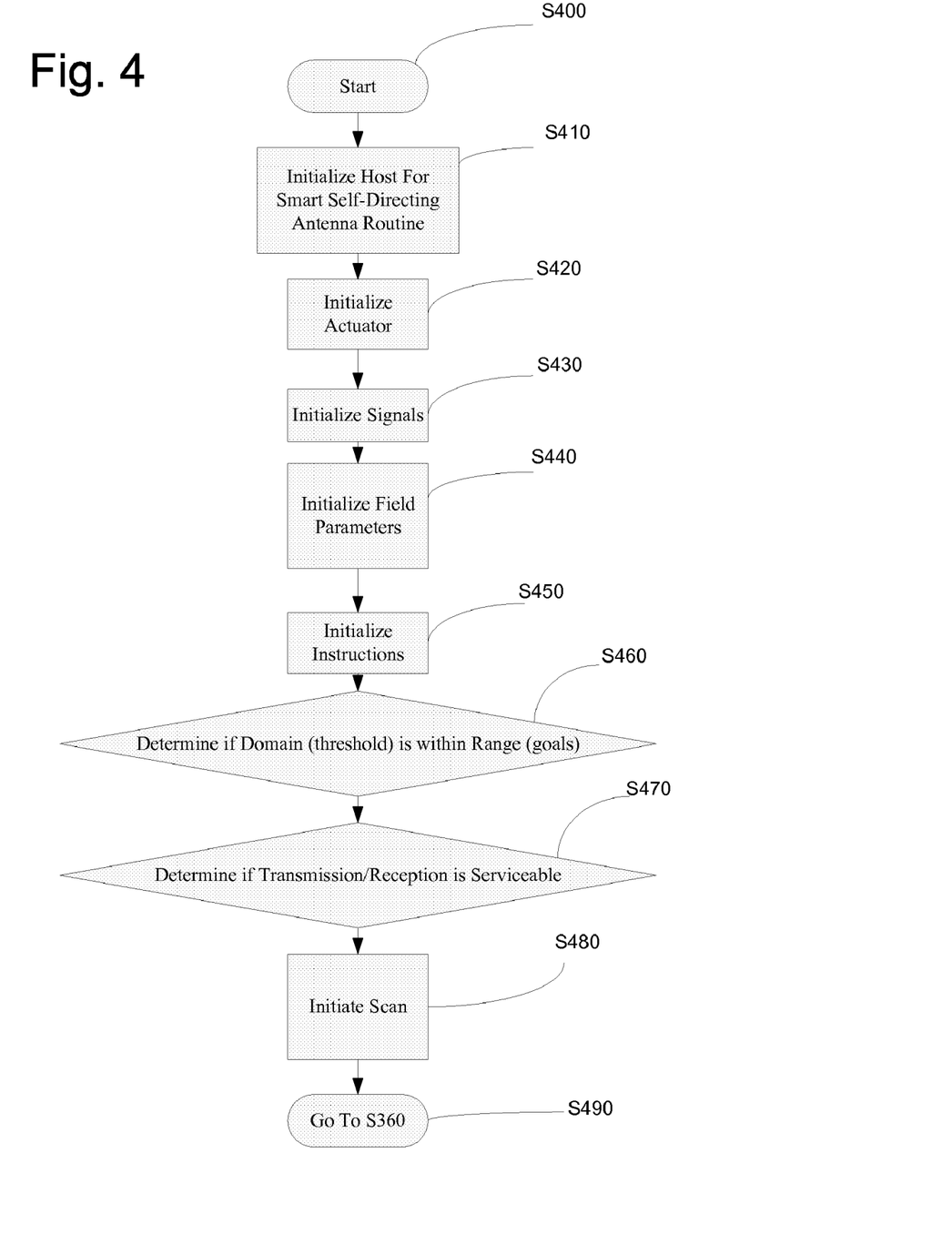
FIG. 4 is a flowchart of an exemplary method to activate a smart self-directing antenna routine for the inventive directional antenna system.

FIG. 4 is a flowchart of an exemplary method to activate a smart self-directing antenna routine for the inventive directional antenna system. As shown in FIG. 4, the process of activation of the smart self-directing antenna routine according to this invention begins at step S400 and immediately continues to step S410.

In step S410 the host computer 130, or similar processor or controller, is initialized, or otherwise activated to manage, direct, and or balance the smart self-directing antenna routine. The initialization may occur when the processor receives a signal from any type of conventional source or triggering event. Further, the initialization may incorporate any type of conventional source or triggering event, known or later developed. After the host computer 130 has been initialized, control continues to step S420.

In step S420, and when the deployment of the inventive directional antenna system includes at least one actuator, the smart antenna actuator 180 or actuators are initialized, or otherwise activated. The antenna actuator 180 may be an actuator or device currently known or later developed. After the actuator 180 is initialized, or in the absence of any actuator control continues to step S430.

In step S430 the communication signals, or similar message, are initialized, and which initialization process may include gathering data from a storage device or register. The communication signals may be a conventional data message, or any other similar method or means currently known or later developed. After the communication signals are initialized, control continues to step S440.

In step S440 the field parameters are initialized, or otherwise turned from an inactive state to an active state, or otherwise sent to the host computer 130. The data contained in the field parameters may include spatial coordinates or similar instructions directed to an individual antenna, or to a group of specific antennae. Further, the field parameters may include a preset register of directions corresponding to specific movement by the actuator 180. After the field parameters are initialized, control continues to step S450.

In step S450 the instruction sets are initialized, or otherwise turned from an inactive state to an active state, or otherwise sent to the host computer 130. The data contained in the instruction set, may for example, direct the directional antenna 120 to move in a certain direction, or set of directions, or similar pattern. After the instruction sets are initialized, control continues to step S460.

In step S460 the determination is made whether operational requirements for the inventive directional antenna system have been reached. The smart antennae routine may balance the need for further positional evaluation with the observed signal strength, and clarity. Other criterion may be used by the smart antenna routine in determining whether further positional evaluation is necessary, or if the measured signal is well within the operational boundaries, the smart antenna routine may end. If in step S460 the determination is not made that the smart antenna routine is required, control continues to step S470.

In step S470 the determination is made whether the observed transmission and reception of RF signals, between the antennae, is serviceable. Beyond operational boundaries, an evaluation may include a test signal sent between the given antennae pair, to establish a connection necessary for data transfer between two sources. If in step S470 the determination is made that the observed transmission and reception signals are serviceable, control continues to step S480.

Contrary, and if the determination is not made that the observed transmission and reception signals are serviceable, a message may be sent to the host computer 130, and or otherwise displayed to an operator, or technician. The operator or technician may then instruct the patient undergoing the x-ray to reposition themselves on the equipment. After the patient undergoing the x-ray is repositioned, control jumps to step S460. Steps S460-S470 are then repeated until a determination is made in step S470 that the observed transmission and reception signals are serviceable.

Control then continues to step S480 and the inventive directional antenna system will receive the signal that it is permissible to scan, or otherwise operate the x-ray equipment for a radiology. After the inventive directional antenna system receives the signal that it is permissible to scan, or otherwise operate the x-ray equipment, control continues to step S490, which sends control back to step S360. Discussions of the steps that follow are found within the description for FIG. 3.

Figure 5:
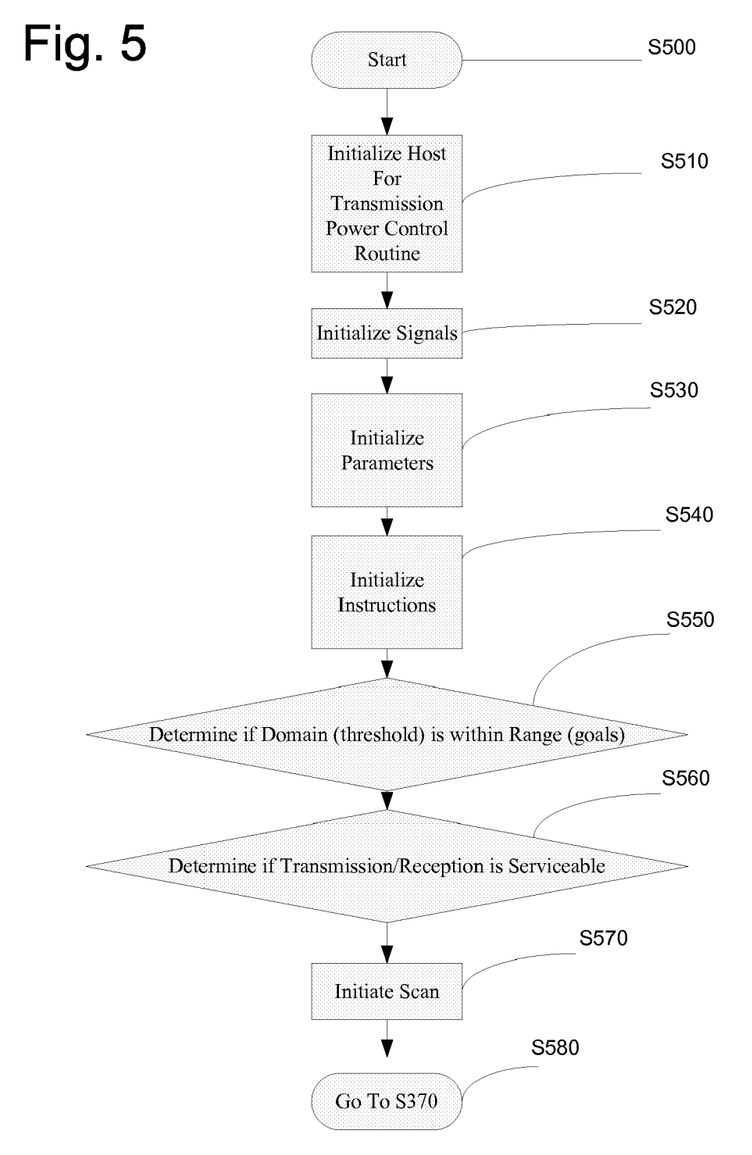
FIG. 5 is a flowchart of an exemplary method to activate a transmission power control routine for the inventive directional antenna system.

FIG. 5 is a flowchart of an exemplary method to activate a transmission power control routine for the inventive directional antenna system. As shown in FIG. 5, the process of activation of the transmission power control routine according to this invention begins at step S500 and immediately continues to step S510.

In step S510 the host computer 130, or similar processor or controller, is initialized, or otherwise activated to manage, direct, and or balance the transmission power control routine. The initialization may occur when the processor receives a signal from any type of conventional source or triggering event. Further, the initialization may incorporate any type of conventional source or triggering event, known or later developed. After the transmission power control routine has been initialized, control continues to step S520.

In step S520 the communication signals, or similar message, are initialized, and which initialization process may include gathering data from a storage device or register. The communication signals may be a conventional data message, or any other similar method or means currently known or later developed. After the communication signals are initialized, control continues to step S530.

In step S530 the field parameters are initialized, or otherwise turned from an inactive state to an active state, or otherwise sent to the host computer 130. The data contained in the field parameters may include power band constraints or similar instructions directed to a license-free, low power wireless environment with an individual antenna, or to a group of specific antennae. Further, the field parameters may include a preset register of directions corresponding to specific power settings and or levels. These specific power settings will be measured against the dynamic real-time power settings, and balanced by the optimal targeted settings. After the field parameters are initialized, control continues to step S540.

In step S540 the instruction sets are initialized, or otherwise turned from an inactive state to an active state, or otherwise sent to the host computer 130. The data contained in an instruction set, may for example, direct the transmission power controller 190 to cycle the power settings in a particular direction, or set of directions, for example to boost or to diminish power, or the like. After the instruction sets are initialized, control continues to step S550.

In step S550 the determination is made whether operational requirements for the inventive directional antenna system have been reached. The transmission power routine may balance the need for further power adjustment evaluation with the observed RF signal strength, and clarity. Other criterion may be used by the transmission power routine in determining whether further power adjustment evaluation is necessary, or if the measured signal is well within the operational boundaries, the transmission power routine may end. If in step S550 the determination is not made that the transmission power routine is required, control continues to step S560.

In step S560 the determination is made whether the observed transmission and reception of RF signals, between the antennae, is serviceable. Beyond operational boundaries, an evaluation may include a test signal sent between the given antennae pair, to establish a connection necessary for data transfer between two sources. If in step S560 the determination is made that the observed transmission and reception signals are serviceable, control continues to step S570.

Contrary, and if the determination is not made that the observed transmission and reception signals are serviceable, a message may be sent to the host computer 130, and or otherwise displayed to an operator, or technician. The operator or technician may then instruct the patient undergoing the x-ray to reposition themselves on the equipment. After the patient undergoing the x-ray is repositioned, control jumps to step S550. Steps S550-S560 are then repeated until a determination is made in step S560 that the observed transmission and reception signals are serviceable.

Control then continues to step S570 and the inventive directional antenna system will receive the signal that it is permissible to scan, or otherwise operate the x-ray equipment for a radiology After the inventive directional antenna system receives the signal that it is permissible to scan, or otherwise operate the x-ray equipment, control continues to step S580, which sends control back to step S370. Discussions of the steps that follow are found within the description for FIG. 3.

While this invention has been described in conjunction with the exemplary embodiments outlined above, it is evident that many alternative, modifications and variations will be apparent to those skilled in the art. Accordingly, the exemplary embodiments of the invention, as set forth above, are intended to be illustrative, not limiting. Various changes may be made without departing from the spirit and scope of the invention, and the following claims are intended to cover such modifications and changes.

What is claimed is:

1. A directional antenna system for wireless communication between x-ray apparatus, the system comprising:
   a host computer;
   an x-ray tube with an emission scan channel;
   a first directional antenna connected to the x-ray tube and with an orientation parallel to the emission channel;
   a second antenna wirelessly communicating with the first directional antenna;
   an x-ray detector wirelessly communicating with the x-ray tube; and
   a rigid panel supporting the second antenna and the x-ray detector being in contact with the emission scan channel.

2. A directional antenna system according to claim 1, wherein the first directional antenna has smart antenna characteristics.

3. A directional antenna system according to claim 1, wherein the system has a transmission power routine.

4. A directional antenna system according to claim 1, wherein the first directional antenna has smart antenna characteristics and the system has a transmission power routine.

5. A directional antenna system according to claim 1, wherein the first directional antenna has smart antenna characteristics and proximate to the first antenna or proximate to the second antenna wirelessly communicating with the first antenna, at least one antenna is utilized to determine a communication channel within desired parameters.

6. A directional antenna system according to claim 1, wherein the system has a transmission power routine and proximate to the first antenna or proximate to the second antenna wirelessly communicating with the first antenna, at least one antenna is utilized to determine a communication channel within desired parameters.

7. A directional antenna system according to claim 1, wherein the first directional antenna has smart antenna characteristics and the system has a transmission power routine.

8. A directional antenna system according to claim 4, wherein a radiology patient receives the minimum amount of radiation during an x-ray scan.

9. A directional antenna system according to claim 7, wherein a radiology patient receives the minimum amount of radiation during an x-ray scan.

10. A method of deploying a wireless link to communicate the orientation of a radiology subject, comprising the steps of:
    positioning an x-ray tube with an emission scan channel relative to a radiology patient for the purpose of imaging a targeted area of the radiology patient;
    positioning a first directional antenna connected to the x-ray tube and with an orientation parallel to the emission channel;
    activating a second antenna to wirelessly communicate with the first directional antenna;
    positioning an x-ray detector to wirelessly communicate with the x-ray tube; and
    positioning a rigid panel supporting the second antenna and the x-ray detector being in contact with the emission scan channel.

11. The method of claim 10, further comprising:
    employing a spatial balancing routine for the first directional antenna.

12. The method of claim 11, further comprising:
    employing a power balancing routine for the first directional antenna.

13. The method of claim 12, further comprising the steps of:
    employing a spatial balancing routine for the first directional antenna, and
    employing a power balancing routine for the first directional antenna.

14. The method of claim 13, further comprising:
    employing a balancing technique to prevent interference that would affect other equipment.

* * * * *